(12) United States Patent
Law et al.

(10) Patent No.: US 7,413,869 B2
(45) Date of Patent: Aug. 19, 2008

(54) METHOD FOR DETERMINING POTENCY OF ANTIGENIC PRESENTING CELL BASED VACCINES

(75) Inventors: Ping Law, Bellevue, WA (US); Madhusudan V. Peshwa, Issaquah, WA (US)

(73) Assignee: Dendreon Corporation, Seattle, WA (US)

( * ) Notice: Subject to any disclaimer, the term of this patent is extended or adjusted under 35 U.S.C. 154(b) by 221 days.

(21) Appl. No.: 10/118,392

(22) Filed: Apr. 5, 2002

(65) Prior Publication Data

US 2003/0190682 A1  Oct. 9, 2003

(51) Int. Cl.
*A01N 1/02* (2006.01)
*C12N 5/08* (2006.01)
*G01N 33/50* (2006.01)

(52) U.S. Cl. .................. 435/7.24; 424/93.71; 435/2; 435/372; 435/372.2

(58) Field of Classification Search .............. 424/93.71; 435/2, 7.24, 372, 372.2, 377
See application file for complete search history.

(56) References Cited

U.S. PATENT DOCUMENTS

| | | | | |
|---|---|---|---|---|
| 5,252,556 | A * | 10/1993 | Ardman | 424/185.1 |
| 5,976,546 | A | 11/1999 | Laus et al. | |
| 6,010,905 | A * | 1/2000 | Cohen et al. | 435/372 |
| 6,080,409 | A | 6/2000 | Laus et al. | |
| 6,121,044 | A | 9/2000 | Peshwa et al. | |
| 6,210,662 | B1 * | 4/2001 | Laus et al. | 424/93.1 |
| 6,558,951 | B1 * | 5/2003 | Tomai et al. | 435/377 |
| 7,060,279 | B2 * | 6/2006 | Laus et al. | 424/185.1 |
| 2002/0094545 | A1 * | 7/2002 | Harris et al. | 435/7.21 |
| 2003/0108527 | A1 * | 6/2003 | Seya et al. | 424/93.4 |
| 2004/0033213 | A1 * | 2/2004 | Walker et al. | 424/93.7 |

FOREIGN PATENT DOCUMENTS

WO   WO 01/48154   *  7/2001

OTHER PUBLICATIONS

Laitinen, H.A., Chemical Anallysis, an advanced text and reference, McGraw-Hill Book Company, Inc., 1960, pp. 537-548.*
Austyn, J.M. et al., Dendritic Cells in the Blood Transfusion Effect, *Trans Proc* 19(1):1434 (1987).
Austyn, J.M. et al., Lymphoid dendritic cells, *Immunology* 62:161-170 (1987).
Austyn, J.M. et al., T cell activation by anti-CD3 antibodies: function of Fc receptors on B cell blasts, but not resting B cells, and CD18 on the responding T cells, *Eur J Immunol* 27:1329-1335 (1987).
Caux, C. et al., Characterization of Human CD34+ Derived Dendritic/Langerhans Cells (D-Lc), *Proceedings of the 3rd International Symposium on Dendritic Cells in Fundamental and Clinical Immunology* (Jun. 19-23, 1994) 2:1-5 (1995).
Caux, C. et al., Human Dendritic Langerhans Cells Generated In Vitro from CD34+ Progenitors Can Prime Naïve CD34+ T Cells and Process Soluble Antigen, *J Immunol* 5427-5435 (1995).
Caux, C. et al., Recent advances in the study of dendritic cells and follicular dendritic cells, *Immunol Today* 16:(1)2-4 (1995).
Cui, Y. et al., Targeting transgene expression to antigen-presenting cells derived from lentivirus-transduced engrafting human hematopoietic stem/progenitor cells, *Blood* 99(2):399-408 (2002).
Fong, L. et al., Induction of tissue-specific autoimmune prostatitis with prostatic acid phosphatase immunization: implications for immunotherapy of prostate cancer, *J Immunol* 159:3113-3117. (1997).
Gratama, J.W. et al., Flow cytometric quantitation of immunofluorescence intensity: problems and perspectives, *Cytometry* 33:166-178 (1998).
Hart, D.N.J., et al., Interstitial Dendritic Cells, *Intern Rev Immunol* 6:127-138 (1990).
Henderson, L.O. et al., Terminology and nomenclature for standardization in quantitative fluorescence cytometry, *Cytometry* 33:97-105 (1998).
Hsu, F.J. et al., Vaccination of patients with B-cell lymphoma using autologous antigen-pulsed dendritic cells, *Nat Med* 2(1):52-58 (1996).
Kuciel, R. et al., Characterization of anti-prostatic acid phosphatase monoclonal antibody and its medical significance, *Biotechnol Appl Biochem* 10:257-272 (1988).
Laus, R. et al., Dendritic cell immunotherapy of prostate cancer: Preclinical models and early clinical experience, *Cancer Research Therapy and Control* 111-10 (2001).
Lenkei, R. et al., Performance of calibration standards for antigen quantitation with flow cytometry, *Cytometry* 33:188-186 (1998).
Pacanowski, J. et al., Reduced blood CD123+ (lymphoid) and CD11c+ (myeloid) dendritic cell numbers in primary HIV-1 infection, *Blood* 98(10):3016-3021 (2001).
Reichardt, V.L. et al., Idiotype vaccination using dendritic cells after autologous peripheral blood stem cell transplantation for multiple myeloma—a feasibility study, *Blood* 93(7):2411-2419 (1999).
Schwartz, A. et al., Standardizing flow cytometry: a classification system of fluorescence standards used for flow cytometry, *Cytometry* 33:106-114 (1998).
Small, E.J. et al., Immunotherapy of hormone-refractory prostate cancer with antigen-loaded dendritic cells, *J Clin Oncol* 18(23):3894-3903 (2000).
Steinman, R., The Dendritic Cell System and Its Role in Immunogenicity, *Annu Rev Immunol* 9:271-296 (1991).
Van Schooten, WCA et al., Biological properties of dendritic cells: Implications to their use in the treatment of cancer, *Mol. Med. Today* 3:254-260 (1997).

* cited by examiner

*Primary Examiner*—David A Saunders
(74) *Attorney, Agent, or Firm*—Susan J. Myers Fitch; Peter J. Dehlinger; King & Spalding LLP

(57) ABSTRACT

The present invention discloses methods useful in the preparation of immunostimulatory vaccines which include as one of their components, activated antigen presenting cells which are characterized by having an ability to stimulate a therapeutic T cells response in vivo.

10 Claims, 9 Drawing Sheets

METHOD FOR DETERMINING POTENCY OF ANTIGENIC PRESENTING CELL BASED VACCINES

FIELD OF INVENTION

The present invention relates to methods for quantifying the potency of antigen presenting cells for use in vaccines having the ability to elicit an in vivo T lymphocyte response. This technology will have particular application in the treatment of diseases such as cancer.

REFERENCES

1. Cui Y, Golob J, Kelleher E, Ye Z, Pardoll D, Cheng L (2002) Targeting transgene expression to antigen-presenting cells derived from lentivirus-transduced engrafting human hematopoietic stem/progenitor cells. Blood 99:399.
2. Pacanowski J, Kahi S, Baillet M, Lebon P, Deveau C, Goujard C, Meyer L, Oksenhendler E, Sinet M, Hosmalin A (2001) Reduced blood CD123+ (lymphoid) and CD11c+ (myeloid) dendritic cell numbers in primary HIV-1 infection. Blood 98:3016.
3. Van Schooten W C A, Strang G, Palathumpat V (1997) Biological properties of dendritic cells: Implications to their use in the treatment of cancer. Mol. Med. Today 3:254.
4. Laus R, Ruegg C L, Wu H Y (2000) Immunostimulatory method. U.S. Pat. No. 06,080,409.
5. Laus R, Ruegg C L, Wu H Y (1999) Immunostimulatory Compositions. U.S. Pat. No. 05,976,546.
6. Fong L, Ruegg C L, Brockstedt D, Engleman E G, Laus R (1997) Induction of tissue-specific autoimmune prostatitis with prostatic acid phosphatase immunization: implications for immunotherapy of prostate cancer. J Immunol 159:3113.
7. Small E J, Fratesi P, Reese D M, Strang G, Laus R, Peshwa M V, Valone F H (2000) Immunotherapy of hormone-refractory prostate cancer with antigen-loaded dendritic cells. J Clin Oncol 18:3894.
8. Laus R, Yang D M, Ruegg C L, Shapero M H, Slagle P H, Small E, Burch P, Valone F H (2001) Dendritic cell immunotherapy of prostate cancer: Preclinical models and early clinical experience. Cancer Research Therapy and Control In press.
9. Kuciel R, Mazurkiewicz A, Ostrowski W S, Stachura J, Steuden I, Szkudlarek J, Radzikowski C (1988) Characterization of anti-prostatic acid phosphatase monoclonal antibody and its medical significance. Biotechnol Appl Biochem 10:257.
10. Reichardt V L, Okada C Y, Liso A, Benike C J, Stockerl-Goldstein K E, Engleman E G, Blume K G, Levy R (1999) Idiotype vaccination using dendritic cells after autologous peripheral blood stem cell transplantation for multiple myeloma—a feasibility study. Blood 93:2411.
11. Hsu F J, Benike C, Fagnoni F, Liles T M, Czerwinski D, Taidi B, Engleman E G, Levy R (1996) Vaccination of patients with B-cell lymphoma using autologous antigen-pulsed dendritic cells. Nat Med 2:52.
12. Laus R, Ruegg C L, Wu H Y (2001) Immunostimulatory composition. U.S. Pat. No. 06,210,662.
13. Henderson L O, Marti G E, Gaigalas A, Hannon W H, Vogt R F, Jr. (1998) Terminology and nomenclature for standardization in quantitative fluorescence cytometry. Cytometry 33:97.
14. Schwartz A, Marti G E, Poon R, Gratama J W, Fernandez-Repollet E (1998) Standardizing flow cytometry: a classification system of fluorescence standards used for flow cytometry. Cytometry 33:106.
15. Gratama J W, D'Hautcourt J L, Mandy F, Rothe G, Barnett D, Janossy G, Papa S, Schmitz G, Lenkei R (1998) Flow cytometric quantitation of immunofluorescence intensity: problems and perspectives. European Working Group on Clinical Cell Analysis. Cytometry 33:166.
16. Lenkei R, Gratama J W, Rothe G, Schmitz G, D'Hautcourt J L, Arekrans A, Mandy F, Marti G (1998) Performance of calibration standards for antigen quantitation with flow cytometry. Cytometry 33:188.

BACKGROUND OF THE INVENTION

Antigen presenting cells (APCs) play a central role in the initiation and expansion of cellular immune responses to cancer and virus infected cells. Foreign antigens are processed by APCs, which then interact with T lymphocytes or other effector cells. Part of the interaction pathway is via co-stimulatory molecules and ligands on APC and T cell surfaces. Currently, numerous clinical trials have been undertaken to test the feasibility and efficacy using antigen presenting cells (APCs) for therapeutic purposes. There are many types of APCs [1,2]. Different types of APCs differ in the origin, concentration in circulation, and the capacity to present antigens (Steinman, et al., Ann. Rev. Immunol. 9: 271 (1991); Caux et al., Immunol Today. 16(1):2-4 (1995); Hart and Mckenzie, Int Rev Immunol. 6(2-3):127-38 (1990); Austyn, Immunology 62(2):161-70 (1987)). The goal of vaccine therapy is to collect APCs or precursors, activate the cells using tumor antigen(s), and infuse the antigen-loaded cells to stimulate a T-cell immune in the patients that is sufficiently potent to cause regression of tumor. APCs have limited capability to kill tumor cells directly, but they can stimulate effector cells such as cytotoxic T cells and natural killer cells to destroy tumor cells. The most common procedure involves harvesting of immature APCs from blood, culturing ex vivo to activate the cells against tumor antigens, and infusing the activated cells to the same patient. Compositions and processes for ex vivo culture of APCs are disclosed in U.S. Pat. No. 6,121,044, incorporated herein by reference.

Blood APCs have several processing characteristics that make them ideal for development of commercial APC-based vaccines. They require only short-time culture (approximately 1 to 2 days) compared to the 7 days or more for APCs derived from monocytes or stem cells, and they do not require cytokines such as IL-4 or GM-CSF for maturation. Both of these characteristics make blood APCs substantially less complex and expensive to produce [3].

Two general processes occur during preparation of ex vivo antigen-loaded APCs for immunotherapy: (1) antigen processing; and (2) APC maturation. The first step in preparing a APC-based vaccine from blood APCs is to harvest immature blood APCs by methods known in the art such as by a standard mononuclear cell leukapheresis. Immature APCs effectively take up and process antigen, but are ineffective at presenting antigen to T cells because they lack cell surface costimulatory molecules and the capacity to secrete immunomodulatory cytokines that are essential to optimize T-cell activation. Thus, immature APCs must mature or become activated before they can effectively stimulate a T-cell-mediated immune response. Accordingly, immature APCs are cultured with an antigen under conditions to yield activated APCs. Various means for antigen delivery are disclosed in U.S. Pat. Nos. 5,976,546 and 6,210,662, incorporated herein by reference. After the activated APCs are washed to remove any unprocessed antigen, the activated APCs are subjected to a series of quality control tests including a determination of the potency of the APCs. The potency of dendritic cells is typically measured by their capacity to activate T cells and induce T cell proliferation. Activation can be monitored by upregulation of cell surface markers such as CD40, CD54, CD80 and CD86 or by increased functional potency using such assays as allogenic mixed lymphocyte reactions (alloMLR).

Current methods of measuring the potency of the APCs utilize five to seven day bioassays which do not provide for "real-time" assessment of product potency. Accordingly, there is a need for techniques for the rapid identification of the potency of activated APCs that have the ability to elicit an immune response. This will, in turn, ensure that sufficient therapeutic quantities of active cells are infused into the patients, which is of importance in the design of therapeutic strategies in relation to disease such as cancer.

SUMMARY OF THE INVENTION

Accordingly, the present invention discloses methods for monitoring the upregulation of cell surface markers which are indicative of APC activation. Activated APCs are appropriate for use in therapeutic composition such as cell based vaccines. The invention, therefore, concerns generally methods useful in the preparation of immunostimulatory vaccines which include as one of their components, APCs which are characterized by having an ability to stimulate a therapeutic T cells response in vivo.

The present invention provides a method for evaluating the potency of an autologous antigen pulsed APC-based vaccine. Thus in one aspect, the invention provides a method for identifying that cell induction has occurred after APC precursors have been activated by incubating the precursors ex vivo with an agent effective to induce the development of the APC precursors to APCs characterized by an ability to stimulate a therapeutic T cell response in vivo. The improvement for identifying that cell induction has occurred at a therapeutically effective level comprises:

a) prior to activating the APC precursors, measuring the mean fluorescence intensity (MFI) of a cell surface marker associated with APC precursors, and selected from the group consisting of CD54, CD1a, CD11b, CD11c, CD40, CD80, CD83, CD86, CD123, HLA class I, HLA class II and combinations thereof;

b) following the induction, measuring the MFI of the same surface marker(s) in activated APCs; and c) if the measured MFI of the surface marker(s) following activation increases a statistically significant amount above the level measured prior to activation, identifying the cells as having been induced to the desired therapeutically effective level.

Other aspects and features will be in part apparent and in part pointed out hereinafter.

BRIEF DESCRIPTION OF THE DRAWINGS

These and other features, aspects, and advantages of the present invention will become better understood with regard to the following description, claims and accompanying drawings where:

FIGS. 2A, 2C, 2E and 2G represent levels of CD54, CD86, CD40 and HLA-DR expression at day 0 (before activation), respectively. FIGS. 2B, 2D, 2F and 2H represent levels of CD54, CD86, CD40 and HLA-DR expression at day 2 (after activation), respectively.

FIGS. 5A and 5D are dot plots of cell size (FSC) versus LDS751 on cells stained with CD54 and isotype control antibody. The region in the panels is defined to exclude debris (events with small size), RBC and platelets (not stained with LDS751) (FIGS. 5B and E). Events included in the region of 5A and 5D were shown with CD54 (FIG. 5B) or isotype staining (FIG. 5E) vs. cell size. Two additional regions were defined: one with large cells positive for CD54 staining, "Large CD54$^+$ Cells", on FIG. 5B, and the other on large cells, "Large IgG2b+ cells" of FIG. 5E.

FIGS. 5C and 5F are CD54 (1:1) staining histograms of events within "Large CD54$^+$ Cells" defined in FIG. 5B is shown in FIG. 5C with the corresponding isotype control histogram in FIG. 5F. Mean Fluorescence Intensity (MFI), shown "Geo Mean", was then used to calculate the number of APC surface CD54 molecules (described in Example 4)

FIGS. 6A and D are dot plots of cell size (FSC) versus LDS751 on cells stained with CD54 and isotype control antibody. The region in the panels is defined to exclude debris (events with small size), RBC and platelets (not stained with LDS751).

FIGS. 6B and E depict the events included in the region of FIGS. 6A and D were shown with CD54 (FIG. 6B) or isotype staining (FIG. 6E) vs. cell size. Two additional regions were defined: one with large cells positive for CD54 staining, "Large CD54$^+$ Cells", on FIG. 6B, and the other on large cells, "Large IgG2+ cells" of FIG. 6E.

FIGS. 6C and 6F depict CD54 (1:1) staining histograms of events within "Large CD54$^+$ Cells" defined in FIG. 6B is shown in FIG. 6C with the corresponding isotype control histogram in FIG. 6F. Mean Fluorescence Intensity (MFI), shown Geo Mean, was then used to calculate the number of APC surface CD54 molecules (described in Example 4.

DETAILED DESCRIPTION

Figure 1:
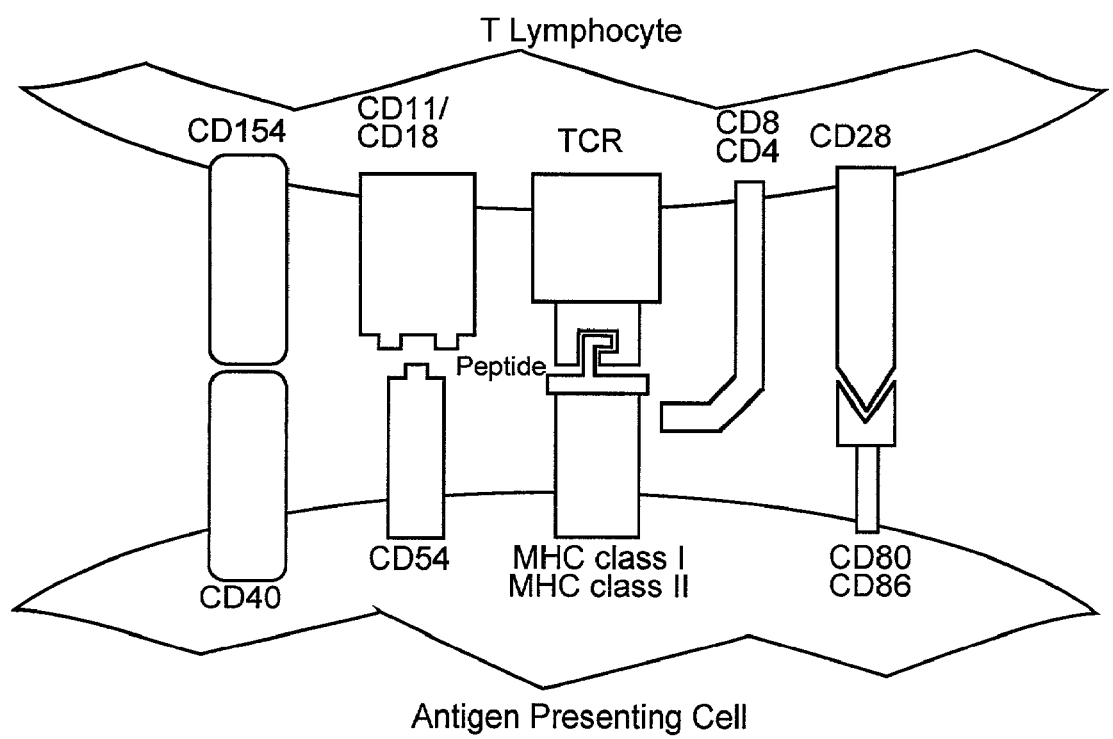
FIG. 1 depicts the co-stimulatory molecule upregulation on DC is required for antigen (peptide-MHC complexes) presentation to T cells.
Figure 2A:
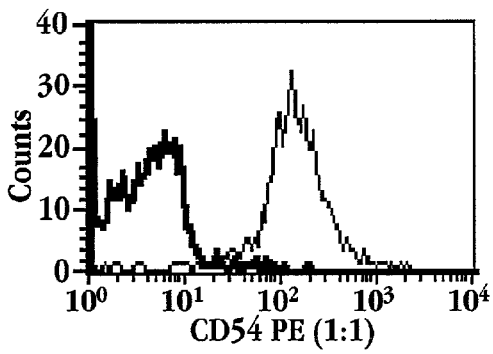
FIGS. 2A through 2H are graphical illustrations that the increase in T cell stimulatory function following APC maturation correlates with upregulation of co-stimulatory molecules on APC.
Figure 2B:
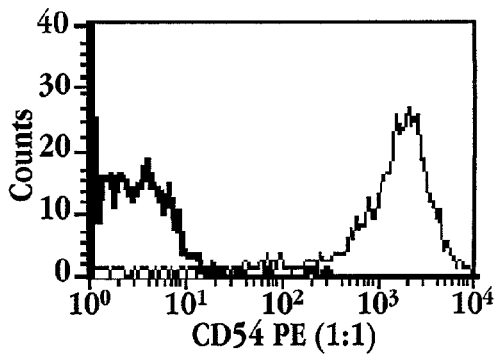
Figure 2C:
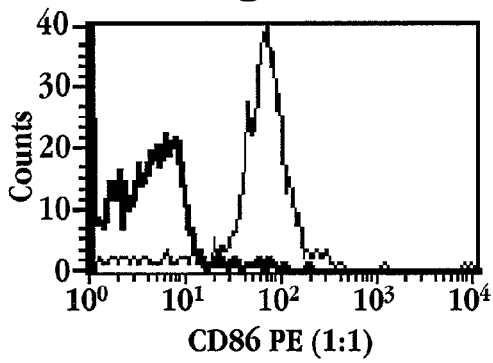
Figure 2D:
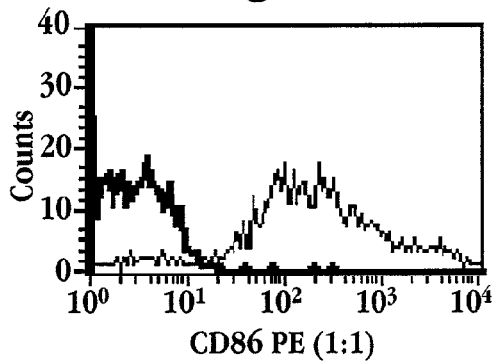
Figure 2E:
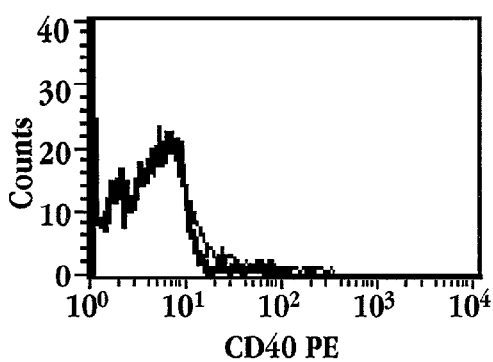
Figure 2F:
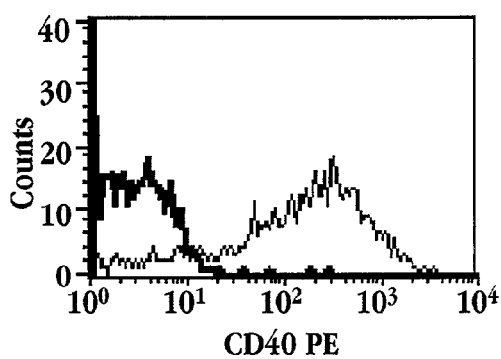
Figure 2G:
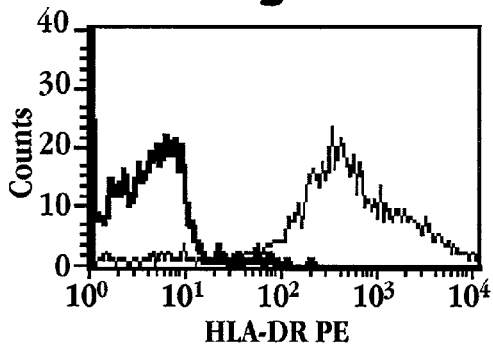
Figure 2H:
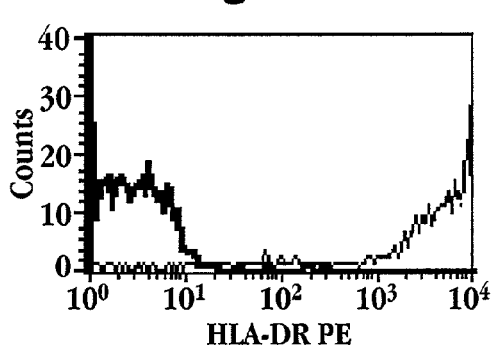

All publications, patents, patent applications or other references cited in this application are herein incorporated by reference in their entirety as if each individual publication, patent, patent application or reference are specifically and individually indicated to be incorporated by reference.

Definitions and Abbreviations:

"Antigen presenting cells" (APC) are cells that are capable of activating T cells, and include, but are not limited to, certain macrophages, T cells, B cells hematopoietic progenitor cells, and dendritic cells.

The term "dendritic cell" refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood, as described herein.

"Potent antigen presenting (PAP) cells" are cells which, after being pulsed with an antigen, can activate naive $CD8^+$ cytotoxic T-lymphocytes (CTL) in a primary immune response.

The phrase "statistically significant amount" when used with regard to the increase in the MFI of the selected cell surface marker refers to the level of upregulation of the cell surface marker which indicates that the APC is activated for use in an APC based vaccine. The statistically significant amount increase is determined by taking a number of the selected cell surface markers measured from a large number of patients and healthy donor samples, preferably more than 50 samples, and determining the standard deviation. The use of the mean plus three times standard deviations as a cut-off results in the determination of the statistically significant amount, i.e., the level of the cell surface marker that should be upregulated prior to releasing cells in a vaccine for infusion. In the case of cell surface marker CD54, the statistically significant amount will fall between approximately 1.5 and 22.0. In the case of cell surface marker CD86, the statistically significant amount will fall between approximately 1.2 and 75.0. In the case of cell surface marker CD40, the statistically significant amount will fall between approximately 2.0 and 150.0. In the case of cell surface marker HLA-DR, the statistically significant amount will fall between approximately 2.0 and 20.0.

Accordingly, the present invention discloses methods for monitoring the upregulation of cell surface markers such as CD54, CD40, CD80, and CD86 which are indicative of APC activation. Activated APCs are appropriate for use in therapeutic composition such as dendritic based vaccines. The invention, therefore, concerns methods useful in the preparation of immunostimulatory vaccines which include as one of their components, APCs which are characterized by having an ability to stimulate a therapeutic T cells response in vivo.

The assay provides the following advantages not known in the prior art: (i) the ratios of the cell surface molecules correlate with antigen presenting function thereby indicating the ability of the activated APCs to induce an immune response; and (ii) the assay can be completed within hours of collecting the APCs from the patient thereby providing the ability to quantitate the potent APCs in the clinical setting prior to releasing the cells for infusion.

The technique for monitoring the APCs starts with the isolation of APC precursors from the patient's blood. The APC precursors are autologous, i.e., obtained from the patient, and are preferably isolated from blood, and more preferably, isolated from peripheral blood, bone marrow or cord blood. In another embodiment, the antigen presenting cells may be isolated from Langerhans cells, tissue dendritic cells, or stem cells. In a preferred embodiment, the antigen cell precursors are dendritic cell precursors, which are isolated from human peripheral blood.

Various APC surface molecules are upregulated during activation and therefore, associated with antigen presentation and is used as a marker to indicate cell activation. Accordingly, after the APC precursors are isolated, mean fluorescence intensity (MFI) of a cell surface marker is measured. Preferably, the cell surface marker measured is CD54, CD1a, CD11b, CD11c, CD40, CD80, CD83, CD86, CD123, HLA-DR, HLA Class I, HLA Class II and combinations thereof. In a preferred embodiment, the cell surface marker being measured is CD86, CD54, CD40, HLA-DR or combinations thereof, more preferably, CD54 or CD86, and most preferably, CD54. The MFI is measured using methods known by those in the art. Preferred methods of measuring MFI are flow cytometry, immunocytochemistry, fluorescence intensity measurement by fluorometer, and any methods known in the art to detect antigen-antibody binding. In a preferred embodiment, the MFI of a cell surface marker is measured first staining the cells with an antibody to the surface marker under conditions which allow for specific binding and correlating the MFI to the number of cell surface markers expressed, preferably using flow cytometry. In a more preferred embodiment, the MFI of cell surface marker CD54, CD86, CD40 or HLA-DR is measured prior to induction.

After the MFI of the selected cell surface marker(s) are measured, the cells are then exposed to a therapeutic agent effective to induce the development of the precursors to mature APCs. Preferably, the therapeutic agent is an activation cassette containing an antigen conjugated to a targeting element, preferably, GM-CSF, which enhances antigen uptake and processing by APCs. In one preferred embodiment, the activation cassette contains prostatic acid phosphatase (PAP) conjugated to GM-CSF (PROVENGE™). In another preferred embodiment, the therapeutic agent is MYLOVENGE™, which contains autologous serum from a patient used as an activation antigen. In another preferred embodiment, the therapeutic agent is an activation cassette containing part of the Her2/Neu molecule combined with GM-CSF, which is known as BA7072. In a preferred embodiment, the cells are cultured for approximately 40 hours in serum-free medium with an activation cassette.

Figure 4A:
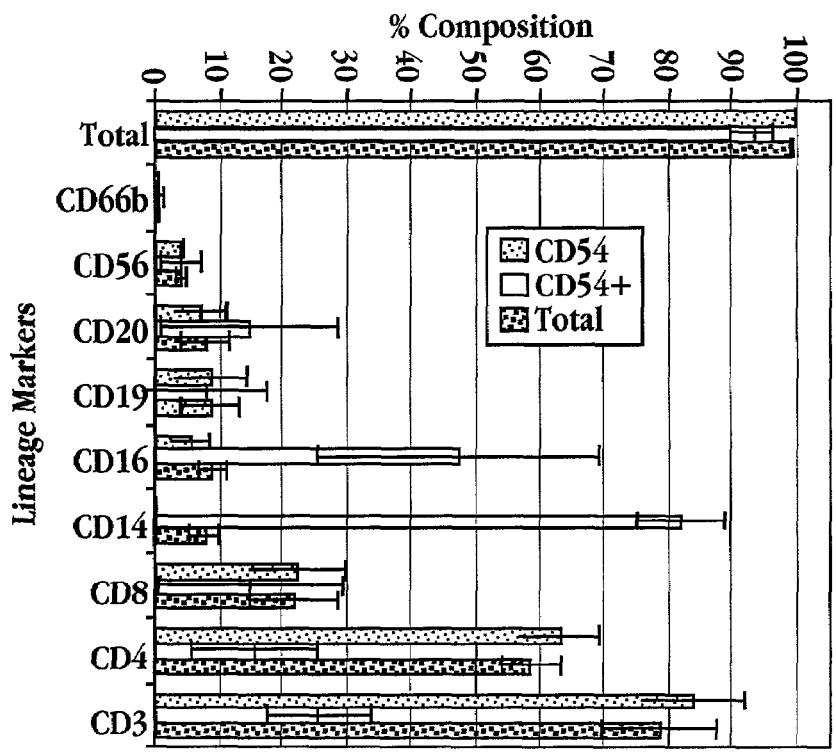
FIGS. 4A and 4B are graphs which illustrate the co-expression of other markers on CD54$^+$ cells.
Figure 4B:
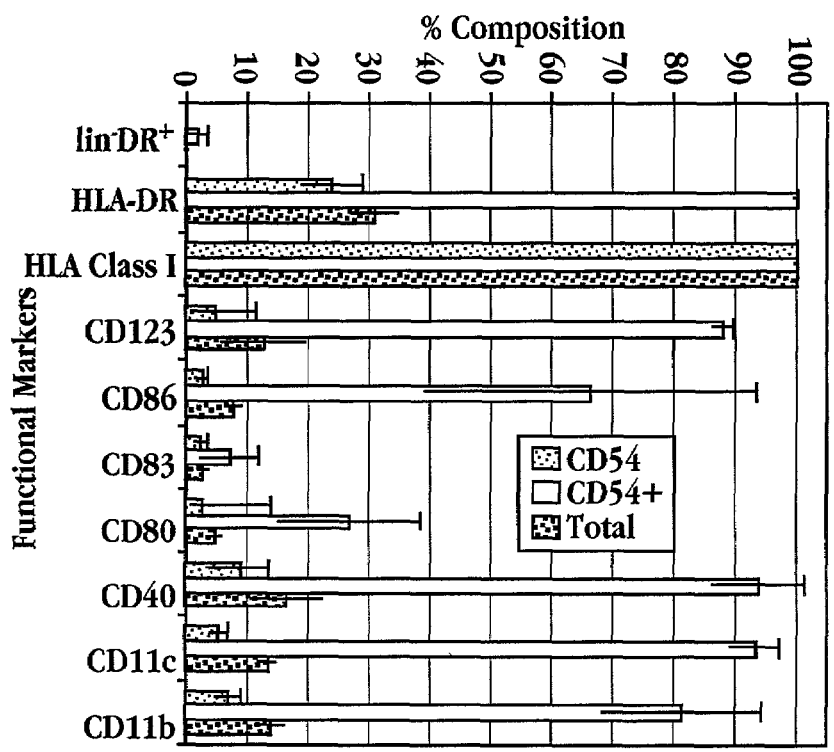
Figure 5A:
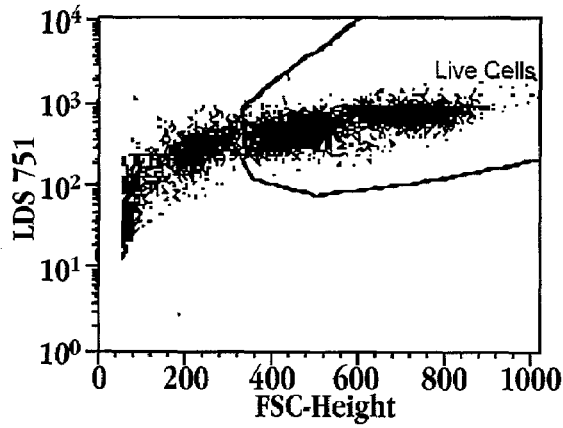
FIGS. 5A to 5F are flow cytometry graphs of APC precursors prior to culture activation.
Figure 5D:
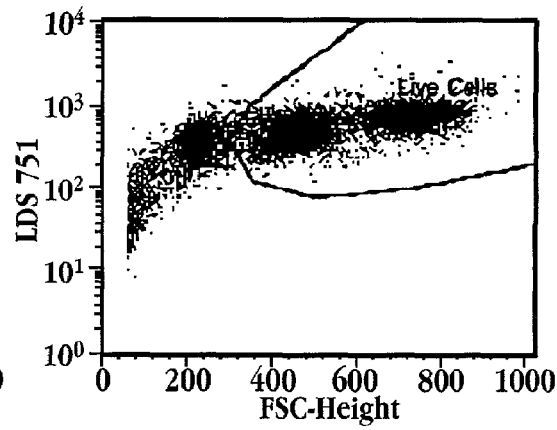
Figure 5B:
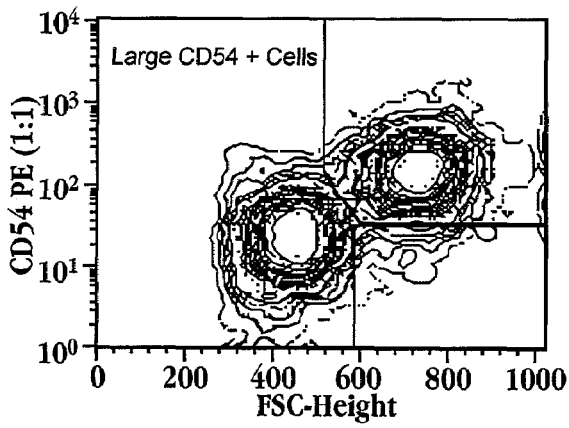
Figure 5E:
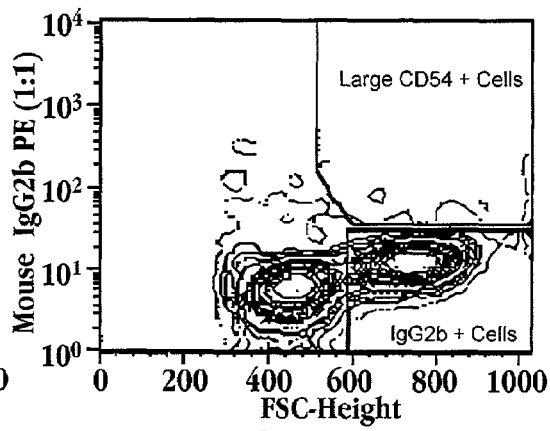
Figure 5C:
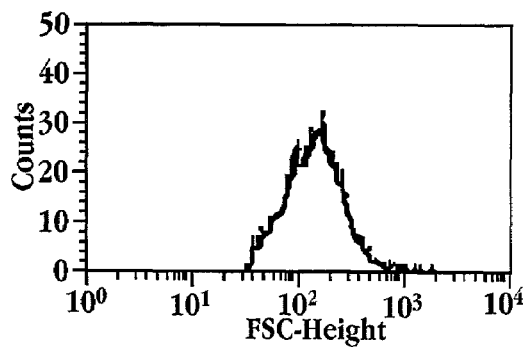
Figure 5F:
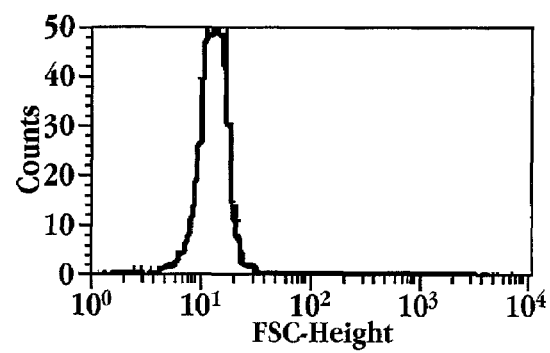
Figure 6A:
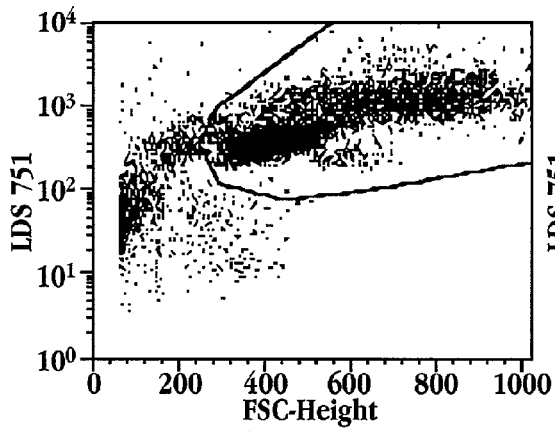
FIGS. 6A to 6F are flow cytometry graphs of APCs after culture activation.
Figure 6D:
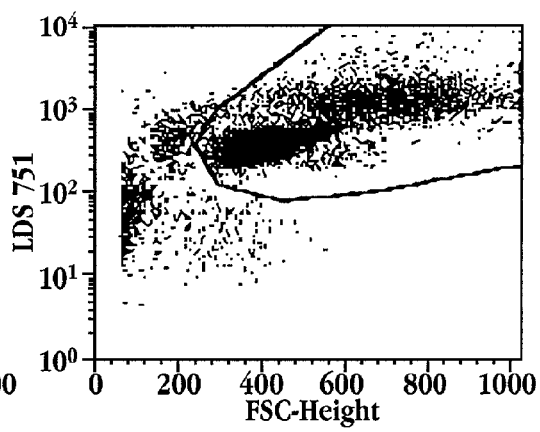
Figure 6B:
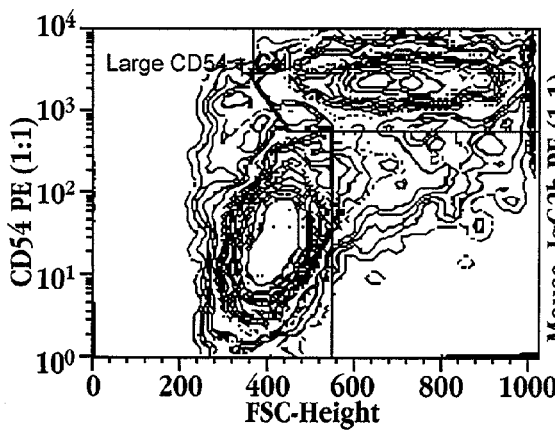
Figure 6E:
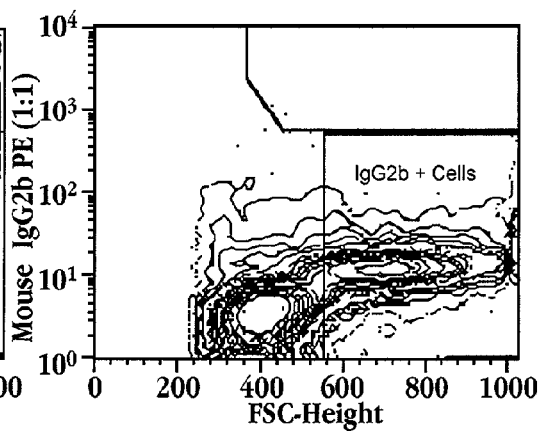
Figure 6C:
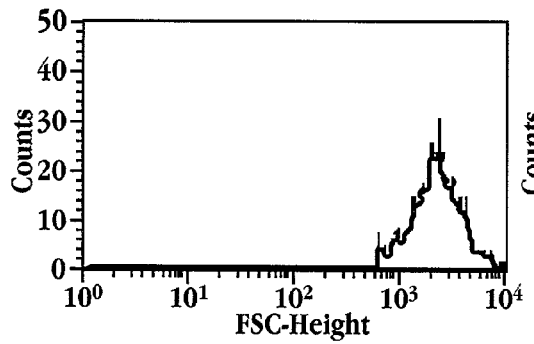
Figure 6F:
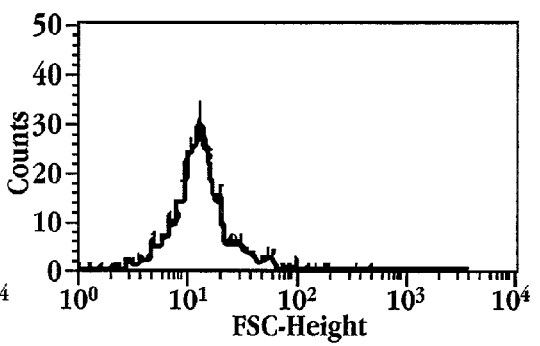

Following exposure of the cell to the therapeutic agent, the MFI of the same cell surface marker is measured in the activated APC. Preferably, the MFI of the cell surface marker is measured within several hours after exposure of the APC to the therapeutic agent thereby allowing for a rapid assay to determine dendritic cell potency. Various APC surface markers are upregulated during the activation process, therefore, the increase in the number or level of surface markers is correlated to cell activation. As shown in FIGS. 4A and 4B, these APC surface markers include but are not limited to, CD54, CD86, CD40 and HLA-DR. When the MFI of the selected cell surface marker measured after induction is a statistically significant amount above the level measured prior to activation, the APC based vaccine is potent for reinfusion back into the patient. The statistically significant amount increase is determined by taking a number of the selected cell surface markers measured from a large number of patients and healthy donor samples, preferably more than 50 samples, and determining the standard deviation. The use of the mean plus three times standard deviations as a cut-off ensures that the upregulation of the marker is not a random event.

In a preferred embodiment, the cell surface markers measured before and after induction of the APC precursor with a therapeutic agent is CD54 or CD86. In one embodiment, the cell surface marker measured before and after induction of the APC precursor is CD54. Preferably, the increase in the MFI of CD54 is approximately between 1.5 and 22.0 fold, preferably between 1.5 and 10 fold, more preferably, between 1.5 and 5 fold, and most preferably, approximately 1.75.

In another preferred embodiment, the cell surface marker measured before and after induction of the APC precursor is CD86. Preferably, the increase in the MFI of CD86 is approximately between 1.2 and 75.0 fold, more preferably, between 1.2 and 20.0 fold, more preferably between 1.2 and 10 fold, even more preferably, between 1.2 and 5 fold, and most preferably, approximately 1.50.

In another preferred embodiment, the cell surface marker measured before and after induction of the APC precursor is CD40. Preferably, the increase in the MFI of CD40 is approximately between 2.0 and 150.0 fold, preferably between 2.0 and 50 fold, more preferably, between 2.0 and 20 fold, and most preferably, approximately 8.0 fold.

In another preferred embodiment, the cell surface marker measured before and after induction of the APC precursor is HLA-DR. Preferably, the increase in the MFI of HLA-DR is approximately between 2.0 and 20.0 fold, more preferably between 2.0 and 5 fold and most preferably, approximately 5.0-fold.

In another preferred embodiment, the cell surface marker measure before and after induction of the APC precursor is CD54 in combination with at least one marker selected from the group consisting of CD86, CD40, and HLA-DR.

The activated APCs which were assayed and determined to be potent can be utilized in a vaccine and reinfused back into the patient. In one preferred embodiment where the APC precursors were exposed to an activation cassette contains prostatic acid phosphatase (PAP) conjugated to GM-CSF (PROVENGE™), the vaccine is preferably used for the treatment of prostate cancer. In another preferred embodiment, where the APC precursors were exposed to MYLOVENGE™, the vaccine is preferably used for the treatment of B-cell malignancies. In another preferred embodiment where the APC precursors were exposed to an activation cassette containing part of the Her2/Neu molecule combined with GM-CSF, the vaccine is preferably utilized for the treatment of tumor cells expressing HER-2/neu, primarily breast, ovarian and colorectal cancer.

Also contemplated within the scope of the invention is the provision of kits for the use of the above method to monitor the upregulation of cell surface markers which are indicative to cell activation for the preparation of immunostimulatory vaccine.

To assist in understanding the present invention, the following examples are included which describe the results of a series of experiments. The following examples relating to this invention should not, of course, be construed in specifically limiting the invention and such variations of the invention which would be within the purview of one skilled in the art are considered to fall within the scope of the present invention as hereinafter claimed.

EXAMPLES

Example 1

Preparation of Human Antigen Presenting Cells (APC)

Human APC were prepared from leukapheresis collection from patients with prostate cancer, multiple myeloma and/or tumors bearing the Her2/neu markers. For experimental studies, leukapheresis products from healthy volunteers were used. APC precursors were obtained by density gradient centrifugation on BDS solutions and devices. Precursor cells were activated by culturing for 40 hours in the presence of tumor antigen. Provenge™, the APC vaccine for treatment of prostate cancer, consists of cells activated by a recombinant fusion protein of prostatic acid phosphatase (PAP) and GM-CSF [4-9]. Mylovenge™, the APC vaccine for treatment of multiple myeloma, consists of cells activated in the presence of autologous serum (idiotype protein) [10,11]. APC8024, the APC vaccine for treatment of breast and ovarian cancers, consists of cells activated by a recombinant fusion protein containing part of Her2/neu and GM-CSF [12]. Samples of cells at various stages of preparation were collected for cell count, viability, phenotype analysis by flow cytometry (including percentages and upregulation of co-stimulatory cell surface markers), and APC function by allogeneic mixed lymphocyte reaction.

Example 2

Staining of Cells

Blocking:

Mouse serum or immunoglobulin was used to block Fc receptors on cell surface. Cell samples were washed by centrifugation to remove the mouse serum. The blocking step is intended to decrease interference by granulocytes, a small fraction of which may remain after APC precursor preparation and APC activation.

RBC Lysing:

Interference by irrelevant cells was minimized by lysing the RBC in cell sample. Typically, lysing was performed at ambient temperature using ammonium chloride or equivalent reagent. Cells are washed by centrifugation. RBC lysing is not required if nuclear or DNA stain (such as LDS751) is used. This lysing step can be applied before or after specific antibody staining.

Antibody Staining

The cell samples were incubated for 20 to 30 minutes in darkness in cold or at ambient temperatures with specific antibody or combinations. Use of antibody combination (2 or more antibodies conjugated with different fluorochromes to stain the same cell sample) may allow identification of APC based two or more cell surface markers. It is commonly used in leukocyte staining to identify subsets of lymphocytes or exclude non-specifically stained cells. The procedure used for staining for single and combination of antibodies is not different. However, mean fluorescence intensity measurement will be affected by compensation setting and the overlap in the emission spectra of the different fluorochromes, thus affecting the accuracy in the determination of number of surface molecules (see below).

Any unbound antibody was removed by thorough washing (2 or more times) using phosphate buffer saline or an equivalent reagent. A nuclear stain, LDS751, may be used to enhance gating around white blood cell populations, and should be added immediately before acquisition.

Proper isotype matched control antibody(ies) were used to account for non-specific binding. The procedures utilized with the control antibody were identical to those described above [13-16].

Stained cell samples are stored in cold and acquired on flow cytometer within 4 hours. It may be to fix the samples after staining using paraformaldehyde at 0.5 to 2%. Fixed samples can be stored for longer duration (1 to 5 days) in cold.

Example 3

Fluorescence Calibration Standard

QuantiBRITE beads were acquired on flow cytometer typically using software from the manufacturer (FACScalibur with Cellquest program). The bead singlet gate on Forward Scatter (FSC) and Side Scatter (SSC) dot plot to include only beads and exclude debris. The markers in the histogram plot are then adjusted to achieve the best representations of the different bead populations. A copy of the "Completed BEAD ANALYSIS" was printed, and the geometric mean fluorescence intensities (Geo Mean) of "Low", "Med-Low", "Med-High" and "High" was used to later generate the fluorescence standard curve, after acquisition of cell samples.

A new Calibration Curve was generated each time the flow cytometer was turned on.

Example 4

Stained Cell Samples

Stained cell samples are acquired using established flow cytometry procedures. Before acquiring and saving the list-mode data files, FSC and FCS settings were adjusted to place all leukocyte major populations (lymphocytes, monocytes and granulocytes) at the center of the dot plot. Threshold on FSC was adjusted to exclude debris. No adjustment on the fluorescent channel containing the fluorochrome of interest was made since the cytometer is calibrated, any change in instrument setting will invalidate the Standard Curve. A total of 10,000 to 50,000 events is saved in list-mode data files, typical target cell population should have >1,000 events.

Analysis and Calculations

Analysis similar to FIG. 6A through 6H is used to determine % of cells in target populations and the mean fluorescence intensity. In the example, LDS751 is used to distinguish nucleated leukocytes from RBC and platelets. Target cells can be gated using FSC and SSC, or marker(s) other than the target molecules. Control (FIGS. 6D-F) and specific antibody stained (FIG. 6A-C) cell samples are compared side-by-side, and geometric mean fluorescence intensity (Geo Mean) for control and antibody stained cell sample is determined in FIGS. 6C and CF.

The fluorescence Calibration Curve is the linear regression of the log-log plot of PE molecules per bead from QuantiBRITE package insert and the geometric mean fluorescence intensity as described in Example 3. It is possible to use standard computer software (such as Excel) to simply calculate and obtain slope and intercept. The number of bound specific antibody and control is interpolated from the Calibration Curve. The actual target molecules per cell equals specific binding minus control binding.

The same procedure is used for cells before and after activation. The actual target molecules per cell equals specific binding minus control binding. Table 1 illustrates the actual target molecules per cell before activation and Table 2 illustrates the actual target molecules per cell after activation.

TABLE 1

Day 0 (Before Activation)

| Number of PE molecules per bead from package insert | Geometric mean of bead peaks (linear fluorescence) |
|---|---|
| 1400 | 23.64 |
| 14000 | 249.30 |
| 36600 | 636.37 |
| 182000 | 2938.01 |

| | Geometric mean (linear fluorescence) | Number of PE molecules bound |
|---|---|---|
| IgG2b | 12.34 | 705 |
| CD54 | 137.72 | 8025 |

| | Number of PE molecules bound corrected for background |
|---|---|
| CD54 specific binding | 7350 |

TABLE 2

Day 2 (After Activation)

| Number of PE molecules per bead from package insert | Geometric mean of bead peaks (linear fluorescence) |
|---|---|
| 1400 | 22.10 |
| 14000 | 225.32 |
| 36600 | 578.17 |
| 182000 | 2674.57 |

| | Geometric mean (linear fluorescence) | Number of PE molecules bound |
|---|---|---|
| IgG2b | 25.02 | 1552 |
| CD54 | 1370.98 | 89831 |

| | Number of PE molecules bound corrected for background |
|---|---|
| CD54 specific binding | 88279 |

The ratio of the number of co-stimulatory molecules per cell (value after activation divided by that before activation) was calculated. If the ratio is ≧1.75, up-regulation is considered relevant. The value of 1.75 is chosen from prior experience of $CD54^+$ cell staining and analysis. Typically leukapheresis collections contain monocytes and other cells dimly stained for CD54. The number of cell surface CD54 had been measured from a large number of patient and donor samples (≧100), the standard deviation is approximately 25% of the mean. Use of mean+3 times standard deviations (hence 1.75) as cut-off ensures that the up-regulation of the marker is not a random event.

Example 5

Allogeneic Mixed Lymphocyte Reaction

APC after activation were used as stimulator cells and T lymphocytes from healthy individuals were used as responder cells. AOC were irradiated (30 Gy) and graded doses were co-cultured were performed T lymphocytes ($5 \times 10^4$/well) in 96-well microtiter plates for 6 days at 37° C. in 5% $CO_2$. Wells containing responder cells alone served as a negative control. One μCi of $^3$H-Thymidine is added to each well for the final 20 hours of incubation. Cells from each well were harvested separately and $^3$H-thymidine incorporation was measured using a β-counter. Thymidine incorporation is plotted against APC dose per well and EC-50 (effective APC concentration for 50% stimulation) is calculated.

Example 6

Evaluation of APC Surface Markers

Figure 3:
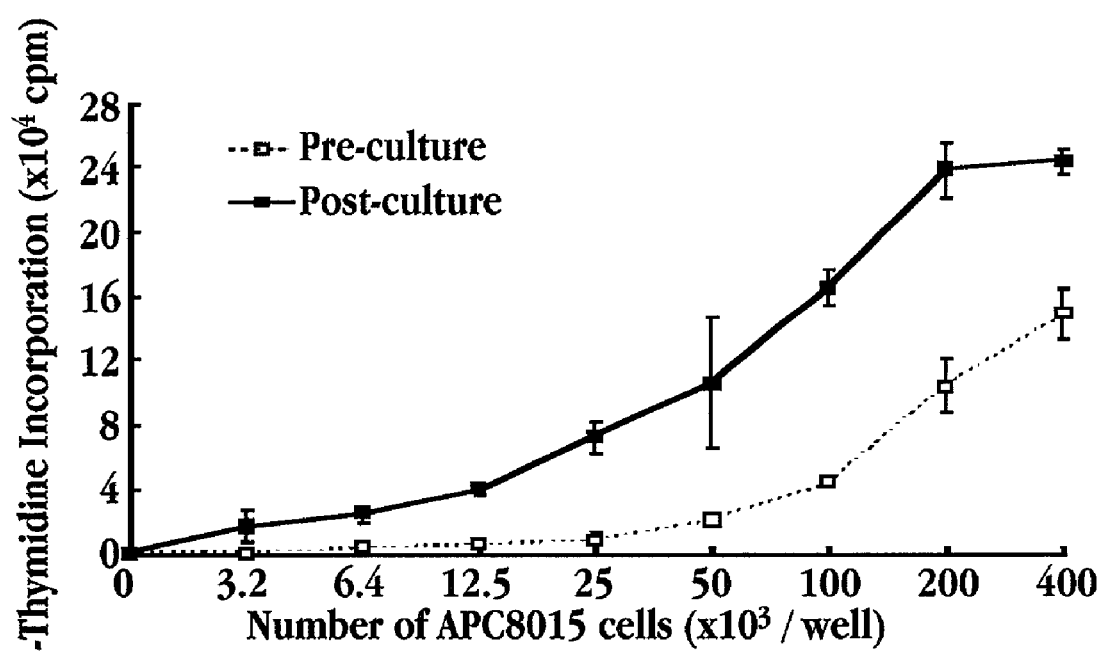
FIG. 3 is a graph illustrating that the increase in T cell stimulatory function following APC maturation correlates with upregulation of co-stimulatory molecule CD54, CD86, CD40, HLA-DR on APCs.

Various APC surface markers are up-regulated during the activation process. As shown in FIG. 3, these include CD54, CD86, CD40, and HLA-DR. CD40 is not expressed without activation. Expression of CD54 and CD86 is low (~$10^2$ on an arbitrary fluorescence scale) before activation and becomes higher after culture ($\geqq 10^3$ for CD54, and ~$3\times10^3$ for CD86). For HLA-DR, expression is already high before activation (~$3\times10^2$) and is off scale ($\geqq 3\times10^3$) post culture.

An increase in the level of cell surface marker is directly related to activation. As shown in Table 3, if APC are not activated, no up-regulation is observed. In a randomized Provenge™ Phase III clinical study, control patients received APC preparation that was not activated with PA2024. Table 3 shows that there is no increase in cell surface CD54 in these non-activated APC.

TABLE 3

Cell Surface CD54 With and Without Activation by PA2024

| | Activation with antigen | Potency (Ratio of CD54$^{Bright}$, Day 2/Day 0) | |
|---|---|---|---|
| | | Mean ± SD | Median |
| Provenge™ Final Product | Yes | 7.8 ± 4.2 | 7.0 |
| Provenge™ Placebo Product | No | 1.0 ± 0.1 | 0.9 |

Summary of CD54 up-regulation of activated and non-activated cells manufactured as part of ongoing phase III clinical trial indicates that the assay is capable of monitoring process consistency
Non-activated cells consisted of APC precursors held at 4° C. for 40 hours without exposure to the prostate tumor antigen (PA2024)

Figure 7:
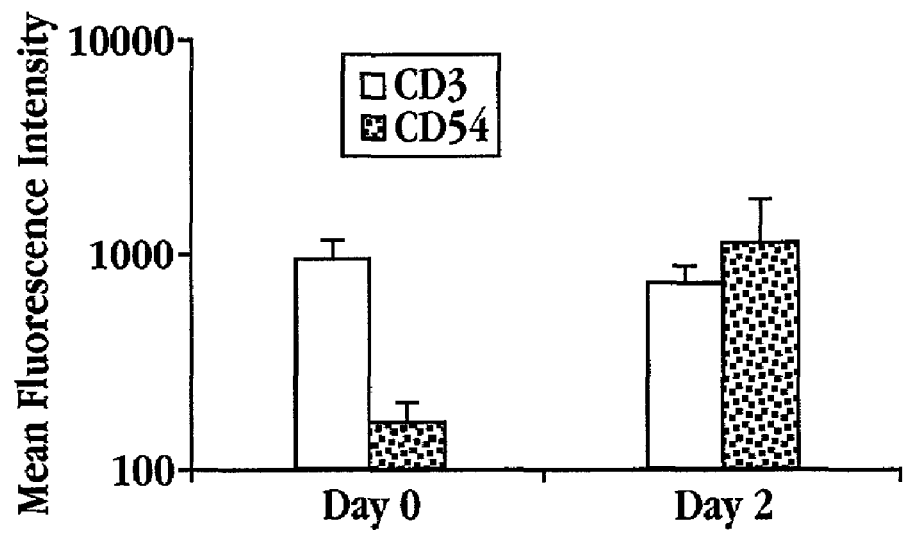
FIG. 7 is a graph illustrating that cell surface marker CD3 which is not related to antigen presentation and is not upregulated by the activation process.

Cell surface markers not related to antigen presentation are not up-regulated by the activation process. FIG. 7 illustrates expression of CD3, a common T lymphocyte surface marker, is not changed between Day 0 and Day 2. CD54 expression is included in the same figure for comparison.

Figure 8:
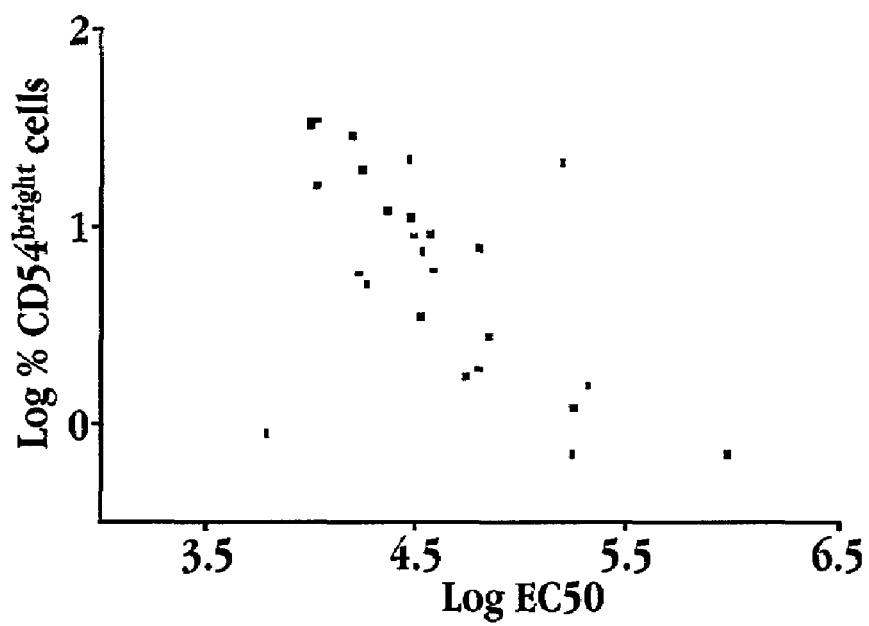
FIG. 8 is a graph illustrating the CD54$^{bright}$ cells and allogeneic T cell stimulation capacity.

Up-Regulation of co-stimulation markers is correlated with the function of antigen presenting cells. Antigen presentation is measured by allogeneic mixed lymphocyte reaction, in which, graded doses of irradiated (30 Gy) APC, as stimulators, are co-cultured with T lymphocytes from different donors, as responders. Proliferation, measured by tritiated thymidine uptake, is directly proportional to the dose of APC in culture. EC-50, effective APC concentration for 50% stimulation can be calculated and is inversely proportional to the APC content in the stimulators. EC-50 values are measured from the infused APC product of patients from Phase II Provenge™ clinical trial and are inversely correlated to the proportion of CD54$^+$ cells, as shown in FIG. 8. The result indicates that APC content is higher, hence a lower cell concentration is required to achieve half maximum stimulation, in products that contained higher percentages of CD54$^+$ cells.

In the currently ongoing Phase III clinical trials for Provenge™, a total of 273 lots was manufactured and infused from the treatment arm. CD54 upregulation averaged to 7.6±4.0 fold (ratio of post and pre culture), with a median of 6.7 (range: 18 to 21.8).

Similar up-regulations on CD54, CD86, CD40 and HLA-DR (post and pre culture activation) are found for Mylovenge (APC product for multiple myeloma) and APC8024 (APC product for breast and ovarian cancers). Table 4 shows the ratio of up-regulation on CD54, CD86, CD40, and HLA-DR for Mylovenge™ manufactured using healthy donor leukapheresis units, and Table 5 is a summary of the CD54 and CD86 up-regulation ratio in 19 clinical lots of APC8024.

TABLE 4

Up-Regulation Ratio of Co-Stimulatory Molecules in Mylovenge™

| N = 4 | CD54 | CD86 | CD40 | HLA-DR |
|---|---|---|---|---|
| Mean ± SD | 4.9 ± 2.0 | 25.8 ± 12.2 | 8.8 ± 7.2 | 5.1 ± 1.2 |
| Median (Range) | 5.4 (2.2-6.6) | 25.8 (14.1-37.6) | 7.9 (1.7 to 17.6) | 5.0 (3.9-6.6) |

TABLE 5

Up-Regulation Ratio of CD54 and CD86 in APC 8024

| N = 4 | CD54 | CD86 |
|---|---|---|
| Mean ± SD | 14.2 ± 7.2 | 28.7 ± 12.8 |
| Median (Range) | 12.4 (7.4-30.7) | 32.3 (1.6-51.9) |

In summary, the results show that co-stimulatory molecules are up-regulated during APC activation. Up-Regulation of surface co-stimulatory molecules is correlated with APC function. The utilization of the upregulatory ratio of one or a combination of these molecules as criteria for clinical lot release testing is based on comprehensive research and development as well as clinical results.

Example 7

Cell Sorting Studies

Figure 9A:
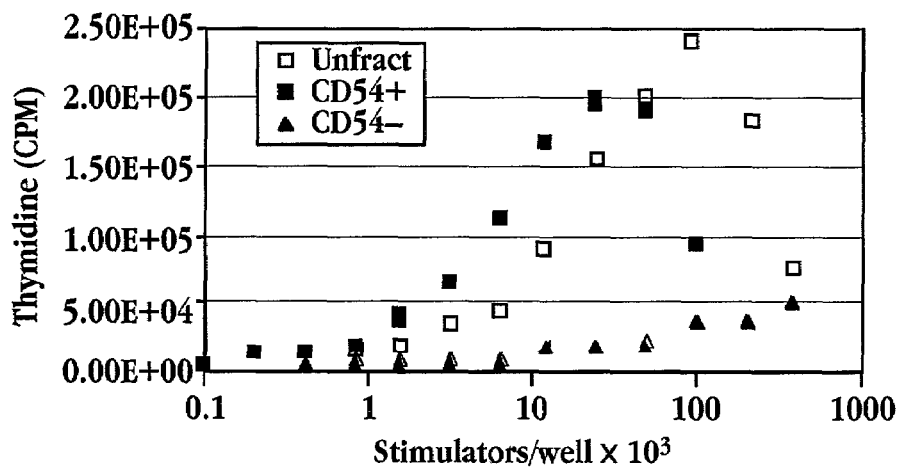
FIGS. 9A and 9C are graphs illustrating that most of the APC in PROVENGE™ is located within the CD54$^+$ cells.
Figure 9B:
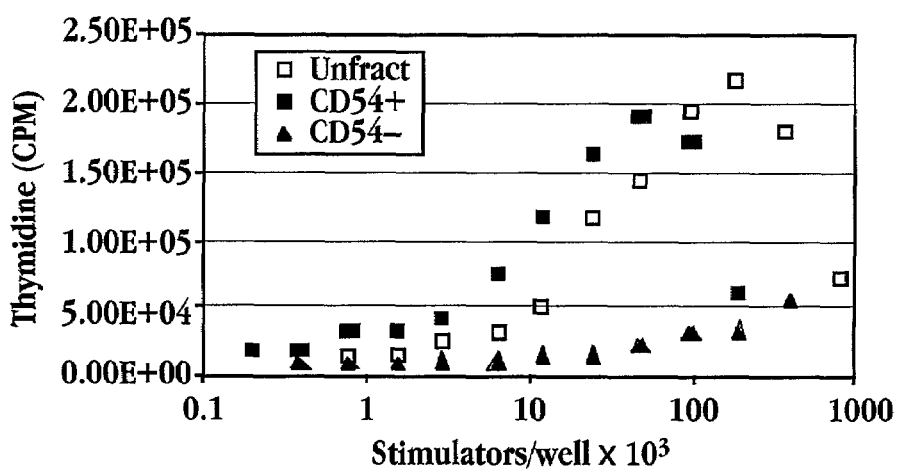
Figure 9C:
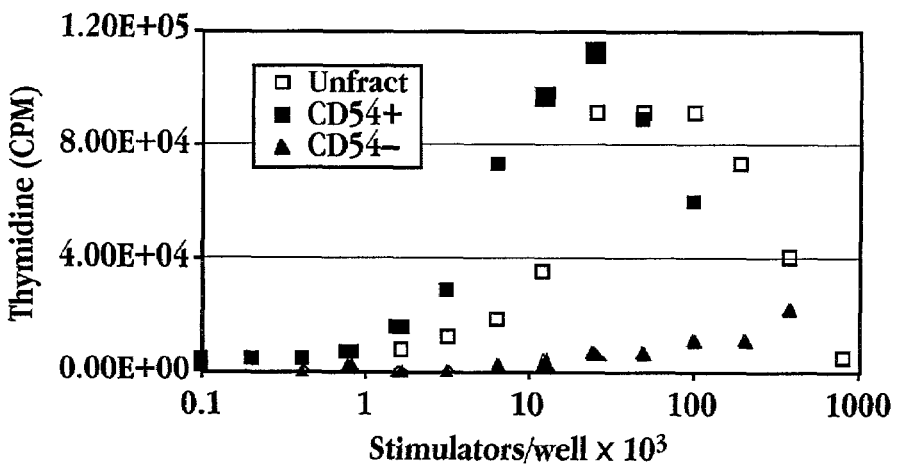

Final APC were sorted according to cell surface expression of CD54 and CD86 using the facility of Fred Hutchinson Cancer Research Center. The cells were prepared stained as described in Example 2 (without LDS751). As shown in FIG. 9, antigen presentation function of sorted cells was assessed by allogeneic mixed lymphocyte reactions as described in Example 5.

Figure 10A:
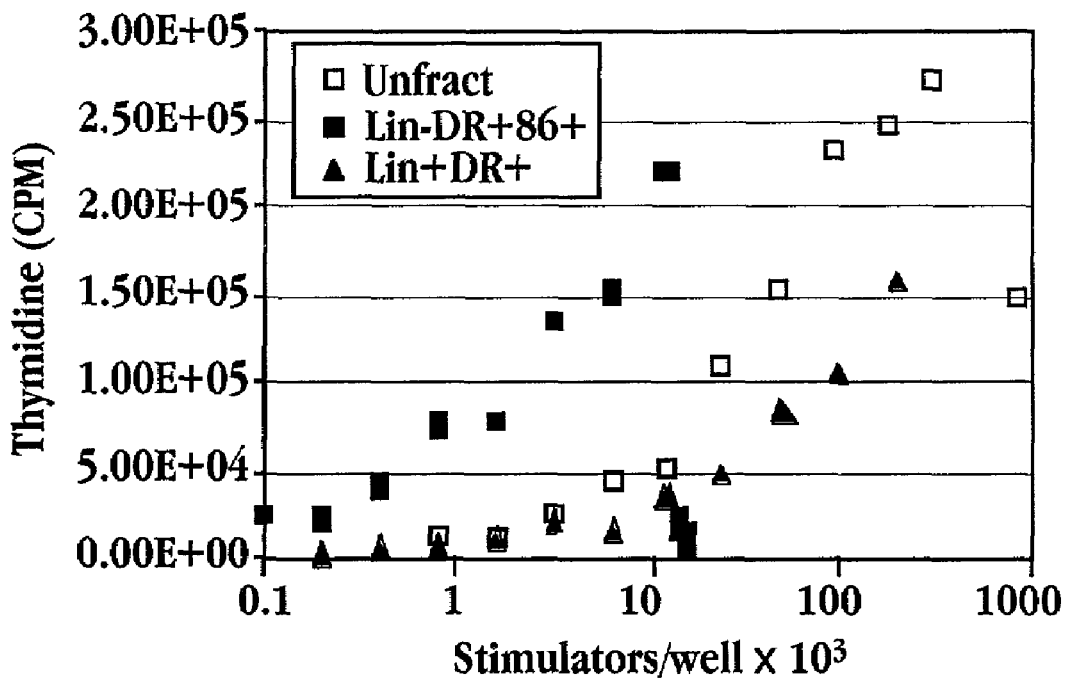
FIGS. 10A-B are graphs illustrating that most of the APC in PROVENGE™ is located within the CD86+ cells.
Figure 10B:
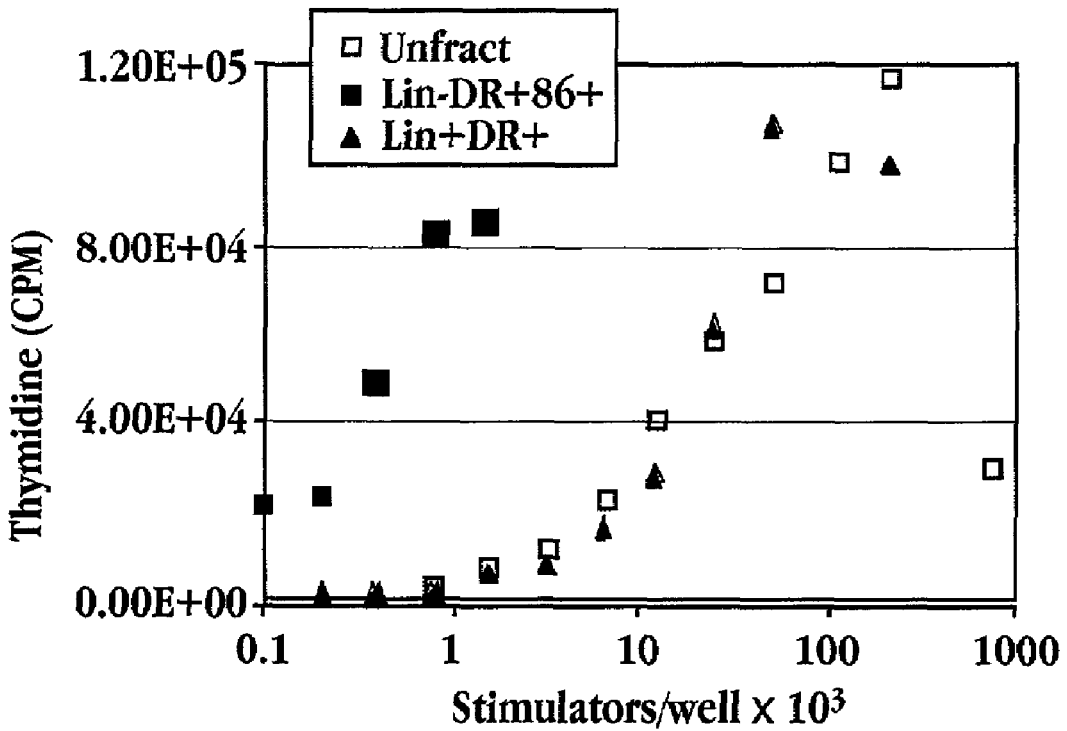

Thus, cultured cells were sorted according to CD54 and CD86 expression. Antigen presenting function was measured by allogenic mixed lymphocyte reaction (MLR), and EC50 (effective concentration for 50% stimulation) was calculated. Significant decreases in EC-50 (paired t-test, p$\leqq$0.05), indicating more potent antigen presenting activities, were observed after sorting for CD54-bright cells (from 1.83±0.4× $10^4$ in the un-sorted control to 6.19±1.94×$10^3$ after sorting) (FIG. 9) or CD86-bright cells (from 3.96±0.30×$10^4$ to 1.52±1.28×$10^3$) (FIG. 10). The results demonstrated that functional blood derived APC can be generated after short-term culture and activation.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A method for determining that antigen uptake has occurred for antigen presenting cell (APC) precursors and cell potency is increased to a therapeutically effective level, comprising:
   (a) prior to activating the APC precursors, measuring the mean fluorescence intensity (MFI) of the surface marker CD54;

(b) incubating the precursors ex vivo with a conjugate preparation of an antigen and GM-CSF effective to activate the development of the APC precursors to antigen presenting cells (APC's), which is characterized by an ability to stimulate a therapeutic T cell response in vivo;
(c) following the activation, measuring the MFI of the same cell surface marker in activated APC's; and
(d) if the measured MFI of the surface marker following activation increases by an amount that is at least three times the standard deviation of the MFI measured prior to activation, identifying the cells as having been activated to a desired therapeutically effective level.

2. The method according to claim 1 in which the measuring of the MFI of the surface marker in both step (a) and (c) comprises:
   (i) staining the cells with an antibody to the surface marker under conditions that allow specific binding; and
   (ii) quantifying the MFI of the surface marker.

3. The method according to claim 2 in which the quantifying is achieved by flow cytometry.

4. The method of claim 1 in which the antigen presenting cells are dendritic cells.

5. The method of claim 4 wherein precursors of the dendritic cells are isolated from human peripheral blood, bone marrow, Langerhans cells or tissue dendritic cells.

6. The method of claim 1 wherein the increase in the MFI of CD54 is approximately between 1.5 and 22.0.

7. The method of claim 1 wherein the increase in the MFI of CD54 is approximately 1.75.

8. A method for clinical lot release testing of dendritic cell-based vaccines, comprising:
   (a) measuring a first mean fluorescence intensity (MFI) of the cell surface marker CD54 in a sample of dendritic-precursor cells;
   (b) exposing the dendritic-precursor cells to a conjugate preparation of an antigen and GM-CSF effective to induce the development of said dendritic-precursor cells;
   (c) measuring a second MFI of the same surface marker; and
   (d) releasing the lot of dendritic cells if the second MFI of the surface marker increases by an amount that is at least three times the standard deviation of the first measured MFI.

9. The method of claim 8 wherein the antigen is prostatic acid phosphatase.

10. The method of claim 8 wherein the antigen is autologous serum from a patient.

* * * * *